Figure 1:
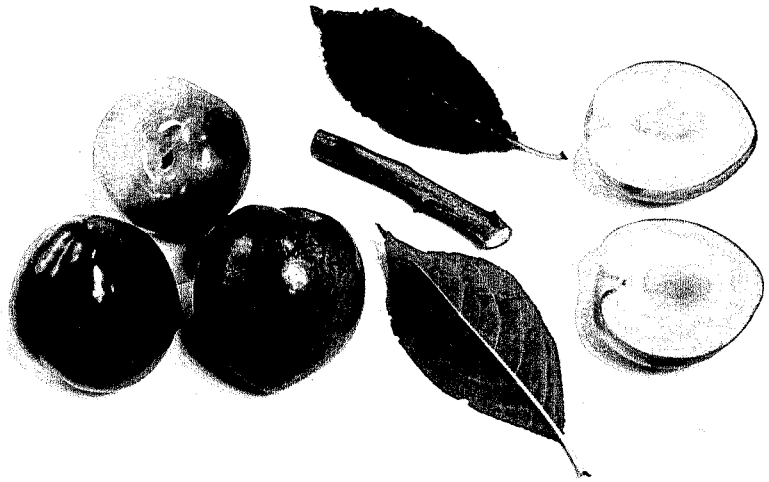

United States Patent [19]

Hengst

[11] Patent Number: Plant 7,348

[45] Date of Patent: Oct. 9, 1990

[54] BILL HENGST OCTOBER GEM PLUM

[76] Inventor: William E. Hengst, 18656 Avenue 296, Exeter, Calif. 93221

[21] Appl. No.: 483,610

[22] Filed: Feb. 21, 1990

[51] Int. Cl.[5] ..... A01H 5/00

[52] U.S. Cl. ..... Plt./38

[58] Field of Search ..... Plt./38

*Primary Examiner*—James R. Feyrer

*Attorney, Agent, or Firm*—Townsend and Townsend

[57] ABSTRACT

A new and distinct Japanese plum tree is disclosed which is characterized by its late maturation. Compared with Casselman, the most similar variety, this new variety matures in Tulare County about 4 weeks later. The fruit is more oblong in shape and is larger than Casselman fruit. The fruit holds well in storage and at room temperature and is suitable for the fresh and dried fruit markets.

1 Drawing Sheet

DESCRIPTION

This invention relates to a new and distinct variety of plum tree *Prunus salicina,* commonly called Japanese Plum, the fruit of which is suitable for the fresh and dried fruit markets.

The new variety is an open pollinated seedling and was discovered by me growing in my plum orchards in Exeter, Calif. in 1986. The new variety, which I call the Bill Hengst October Gem Plum, was reproduced by grafting at 18656 Avenue 296, Exeter, Calif.

The FIGURE illustrates the external views of the fruit of the new variety, a longitudinal sectional view of the fruit of the new variety showing the pit embedded in one-half, two views of a leaf of the new variety, and a side view of a section of branch of the new variety.

PLANT CHARACTERISTICS

The color references listed below refer to the book, *Dictionary of Color,* A. Maerz and M. Rea Paul, McGraw-Hill Book Company, Inc., New York, N.Y., Second Edition, 1950.

The most significant feature of this new variety is that it matures late. In Tulare County in the summer of 1989, October Gem ripened on or about October 1. The most similar variety known to me, Casselman, matured on or about September 1, about four weeks prior to October Gem. The latest maturing variety known to me, Golden Nectar, ripens on or about September 15, two weeks prior to October Gem. The fruit is similar to that of Casselman but is more oblong in shape and is larger than Casselman fruit. The fruit of the new variety is typically about 6 mm larger in diameter than Casselman fruit.

Tree: Medium size, figure upright, productive and regular bearing. The trunk is stocky in relation to length and has medium shaggy surface characteristics. The branches are medium in size and have a medium surface character. They are multi-colored with a base color and lighter colored streaks; the base color of the branches is Mirador (page 39, plate 8, L-6) and the streaks are tan (page 47, plate 12, L-11). The lenticels are few and are about 1×2 mm to 1×4 mm. The leaves are medium having a length of about 92 to 100 mm and width of about 45 to 47 mm; the shape is ovate; the color of the upper surface is Monticello Green (page 69, plate 23, E-11) while the lower surface is SeaSpray (p. 63, plate 20, B-6); the marginal form is double serrate while the glandular characteristics are two to three, opposite or alternate and globose. The petioles are about 13 to 15 mm long and about 2 mm thick. The stem glands number 0 to 2, and are arranged alternate, opposite or on the same side. They are green with a brown center in color, small and are of the globose or reniform type.

Flower Buds: Small, having a short plump shape, and a glabrous surface.

Flowers: First bloom in Tulare County of California occurs on or about March 1, with full bloom about March 10. The flowers are small and white.

Fruit: Reach maturity about October 1 in Tulare County of California, which is about two weeks later than the most similar variety known to me. The fruit is uniformly large in size having a diameter of about 57 to 64 mm, a transverse dimension in suture plane of about 55 to 62 mm and a transverse dimension at right angles to the suture plane of about 62 to 67 mm. The fruit has a uniform form, is ovate and had a distinct, indented suture about 90 to 102 mm long that extends to the pistil point. The ventral surface is rounded and smooth while the stem cavity is acuminate, about 12 mm×18 mm and has a depth of about 5 mm. The base if flat and the apex is prolonged. The pistil point is pointed. The stem is about 12 mm long and has a width of about 2 mm. The skin is thin, has a medium texture, no pubescence and has no tendency to crack. The skin color is Princeton (page 41, plate 9, K-11) with a blush of Malaga (page 37, plate 7, L-1). The flesh color is Princeton (page 41, plate 9, K-11). The surface of the pit cavity is rough and its color is the same as the flesh. The fruit is juicy having a mild sub-acid flavor and no aroma. The texture is meaty and the fibers are moderate, the flesh ripens evenly and has good eating quality, both fresh and dried.

Stone: Cling, length about 25 mm, breadth about 19 mm and thickness about 11 mm. The stone is oval and flattened at the base. The surface sides are rough and the ridges and shallow grooves are near the apex. The ventral edge is thin with a wing near the apex, while the dorsal edge is narrow with shallow grooves throughout. The color is Princeton (page 41, plate 9, K-11).

Kernel: Amygdalin is not present.

Keeping quality of fruit: Good; holds well at storage and at room temperature and has good shipping quality.

Use of fruit: Fresh, market and dried.

I claim:

1. A new and distinct variety of plum tree as described and illustrated and identified by the characteristics enumerated above.

* * * * *